(12) United States Patent
Alexander

(10) Patent No.: US 10,709,805 B2
(45) Date of Patent: Jul. 14, 2020

(54) WALL MOUNTABLE ESSENTIAL OIL DIFFUSER

(71) Applicant: Matthew Aaron Alexander, Orem, UT (US)

(72) Inventor: Matthew Aaron Alexander, Orem, UT (US)

( * ) Notice: Subject to any disclaimer, the term of this patent is extended or adjusted under 35 U.S.C. 154(b) by 0 days.

(21) Appl. No.: 16/160,750

(22) Filed: Oct. 15, 2018

(65) Prior Publication Data

US 2019/0192720 A1   Jun. 27, 2019

Related U.S. Application Data

(60) Provisional application No. 62/610,349, filed on Dec. 26, 2017.

(51) Int. Cl.
*A61L 9/12* (2006.01)
*A61L 9/14* (2006.01)
*F16M 13/02* (2006.01)
*A61L 9/013* (2006.01)

(52) U.S. Cl.
CPC .............. *A61L 9/122* (2013.01); *A61L 9/013* (2013.01); *A61L 9/14* (2013.01); *F16M 13/022* (2013.01); *A61L 2209/111* (2013.01); *A61L 2209/131* (2013.01); *A61L 2209/133* (2013.01)

(58) Field of Classification Search
CPC .................................. A61L 9/14; A61L 9/122
See application file for complete search history.

(56) References Cited

U.S. PATENT DOCUMENTS

| | | | |
|---|---|---|---|
| 7,597,857 B2 * | 10/2009 | Reece | A01M 1/2066 422/124 |
| 9,623,137 B2 | 4/2017 | Chao et al. | |
| 10,034,987 B2 | 7/2018 | Pitcher | |
| 2006/0226251 A1 * | 10/2006 | Helf | A01M 1/205 239/34 |
| 2009/0162253 A1 * | 6/2009 | Porchia | A01M 1/2072 422/124 |
| 2011/0027124 A1 | 2/2011 | Albee et al. | |
| 2011/0049266 A1 | 3/2011 | Jorgensen | |
| 2014/0332990 A1 * | 11/2014 | Brosmith | B01F 3/04085 261/142 |
| 2017/0253338 A1 * | 9/2017 | Fantuzzi | B01F 3/04021 |
| 2018/0099068 A1 * | 4/2018 | Pitcher | A61L 9/14 |

* cited by examiner

*Primary Examiner* — Kevin Joyner
(74) *Attorney, Agent, or Firm* — Superior IP, PLLC; Dustin Call

(57) ABSTRACT

A wall mountable essential oil diffuser. The wall mountable essential oil diffuser includes a housing and a wall dock. The wall dock is configured to attach to a surface and releasably receive at least a portion of the housing. The wall mountable essential oil diffuser also includes an aperture, where the aperture is configured to receive an essential oil container and a fan, where the fan is configured to move air through the aperture and into the essential oil container. The wall mountable essential oil diffuser further includes an outlet, where the outlet is configured to receive a mixture of air and vaporized essential oil and allow the mixture to exit the housing and a switch, where the switch is configured to allow a user to turn on and off the fan.

20 Claims, 6 Drawing Sheets

WALL MOUNTABLE ESSENTIAL OIL DIFFUSER

CROSS-REFERENCE TO RELATED APPLICATIONS

This application claims the benefit of and priority to U.S. Provisional Patent Application Ser. No. 62/610,349 filed on Dec. 16, 2017, which application is incorporated herein by reference in its entirety.

BACKGROUND OF THE INVENTION

An essential oil is a concentrated hydrophobic liquid containing volatile aroma compounds from plants. Essential oils are also known as volatile oils, ethereal oils, aetherolea, or simply as the oil of the plant from which they were extracted, such as oil of clove. Essential oils may be used in aromatherapy, to induce relaxation or to create a scent profile that is pleasing to a user. For this purpose, people often use diffusers, which spread the vaporized oil into a desired environment.

However, many essential oil diffusers suffer from the same drawbacks. In particular, the diffusion mechanism is often complex, requiring a bulky device. Techniques, such as heating the oil, do cause increase the rate of vaporization and consequently the size of the environment into which the essential oil can be diffused. However, this also makes in applicable in many environments. For example, the heat or electronics may create a hazard when used in dry or moist environments, respectively.

In addition, these diffusers often require a horizontal surface in order to operate properly. That is, the diffuser won't work properly unless they are placed on a smooth horizontal surface. While this is acceptable in some environments, other environments lack the space for such placement and/or the horizontal surfaces aren't acceptable for placement of a diffuser.

Accordingly, there is a need in the art for a diffuser that can be used in small environments. In addition, there is a need in the art for the diffuser to be configured to be placed on a non-horizontal surface.

BRIEF SUMMARY OF SOME EXAMPLE EMBODIMENTS

This Summary is provided to introduce a selection of concepts in a simplified form that are further described below in the Detailed Description. This Summary is not intended to identify key features or essential characteristics of the claimed subject matter, nor is it intended to be used as an aid in determining the scope of the claimed subject matter.

One example embodiment includes a wall mountable essential oil diffuser. The wall mountable essential oil diffuser includes a housing and a wall dock. The wall dock is configured to attach to a surface and releasably receive at least a portion of the housing. The wall mountable essential oil diffuser also includes an aperture, where the aperture is configured to receive an essential oil container and a fan, where the fan is configured to move air through the aperture and into the essential oil container. The wall mountable essential oil diffuser further includes an outlet, where the outlet is configured to receive a mixture of air and vaporized essential oil and allow the mixture to exit the housing and a switch, where the switch is configured to allow a user to turn on and off the fan.

Another example embodiment includes a wall mountable essential oil diffuser. The wall mountable essential oil diffuser includes a housing, where the housing is waterproof and a wall dock. The wall dock is configured to attach to a surface and releasably receive at least a portion of the housing. The wall mountable essential oil diffuser includes also a first aperture, where the first aperture is configured to receive a first essential oil container and a second aperture, where the second aperture is configured to receive a second essential oil container. The wall mountable essential oil diffuser further includes a first fan, where the first fan is configured to move air through the first aperture and into the first essential oil container and a second fan, where the second fan is configured to move air through the second aperture and into the second essential oil container. The wall mountable essential oil diffuser additionally includes a first outlet, where the first outlet is configured to receive a first mixture of air and vaporized essential oil and allow the first mixture to exit the housing and a second outlet, where the second outlet is configured to receive a second mixture of air and vaporized essential oil and allow the second mixture to exit the housing. The wall mountable essential oil diffuser moreover includes a first switch, where the switch is configured to allow a user to turn on and off the first fan and a second switch, where the second switch is configured to allow a user to turn on and off the second fan.

Another example embodiment includes a wall mountable essential oil diffuser. The wall mountable essential oil diffuser includes a housing, where the housing is waterproof and a wall dock. The wall dock is configured to attach to a surface and releasably receive at least a portion of the housing. The wall mountable essential oil diffuser includes also a first aperture, where the first aperture is configured to receive a first essential oil container and a second aperture, where the second aperture is configured to receive a second essential oil container. The wall mountable essential oil diffuser moreover includes the first essential oil container, where at least a portion of the first essential oil container is inserted in the first aperture and the second essential oil container, where at least a portion of the second essential oil container is inserted in the second aperture. The wall mountable essential oil diffuser further includes a first fan, where the first fan is configured to move air through the first aperture and into the first essential oil container and a second fan, where the second fan is configured to move air through the second aperture and into the second essential oil container. The wall mountable essential oil diffuser additionally includes a first outlet, where the first outlet is configured to receive a first mixture of air and vaporized essential oil and allow the first mixture to exit the housing and a second outlet, where the second outlet is configured to receive a second mixture of air and vaporized essential oil and allow the second mixture to exit the housing. The wall mountable essential oil diffuser moreover includes a first switch, where the switch is configured to allow a user to turn on and off the first fan and a second switch, where the second switch is configured to allow a user to turn on and off the second fan. The wall mountable essential oil diffuser moreover includes a motion sensor, where the motion sensor prevents operation of the first fan and the second fan unless motion is detected and a power supply, where the power supply is configured to provide power to at least the first fan, the second fan, and the motion sensor.

These and other objects and features of the present invention will become more fully apparent from the following description and appended claims or may be learned by the practice of the invention as set forth hereinafter.

BRIEF DESCRIPTION OF THE DRAWINGS

To further clarify various aspects of some example embodiments of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION OF SOME EXAMPLE EMBODIMENTS

Reference will now be made to the figures wherein like structures will be provided with like reference designations. It is understood that the figures are diagrammatic and schematic representations of some embodiments of the invention, and are not limiting of the present invention, nor are they necessarily drawn to scale.

Figure 1A:
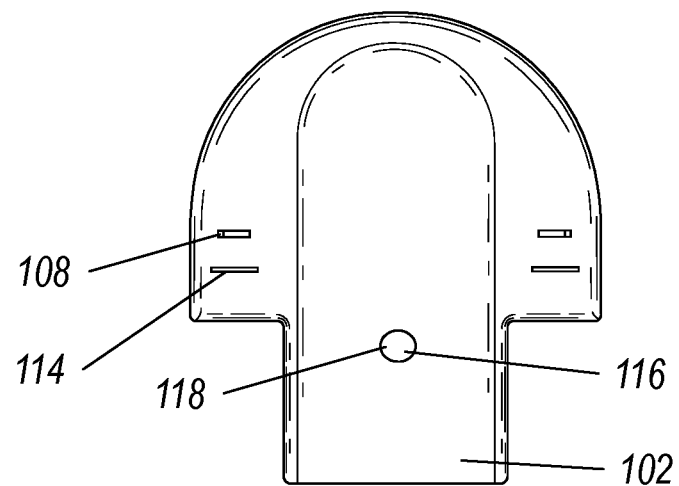
FIG. 1A illustrates a front view of the example of a wall mountable essential oil diffuser.
Figure 1B:
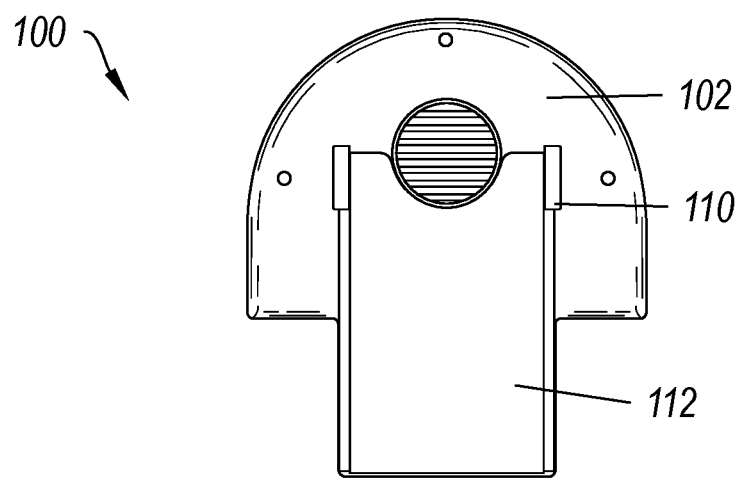
FIG. 1B illustrates a rear view of the example of a wall mountable essential oil diffuser.
Figure 1C:
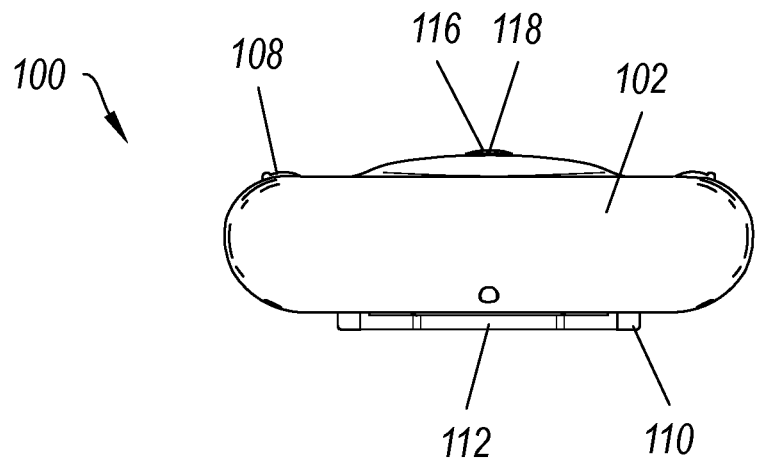
FIG. 1C illustrates a top view of the example of a wall mountable essential oil diffuser.
Figure 1D:
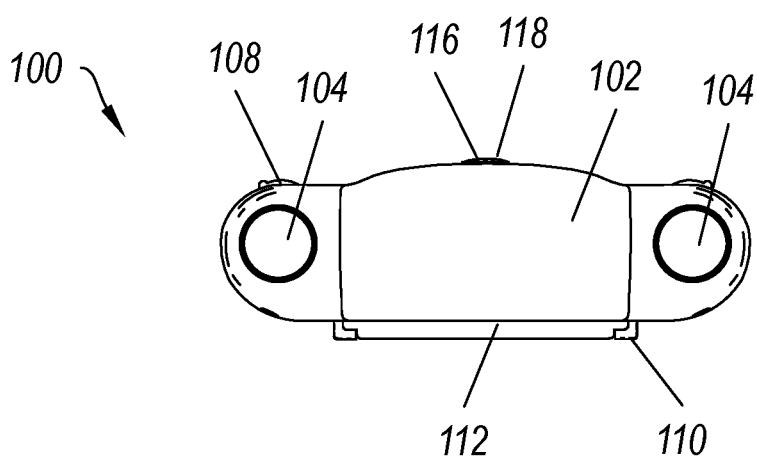
FIG. 1D illustrates a bottom view of the example of a wall mountable essential oil diffuser.
Figure 1E:
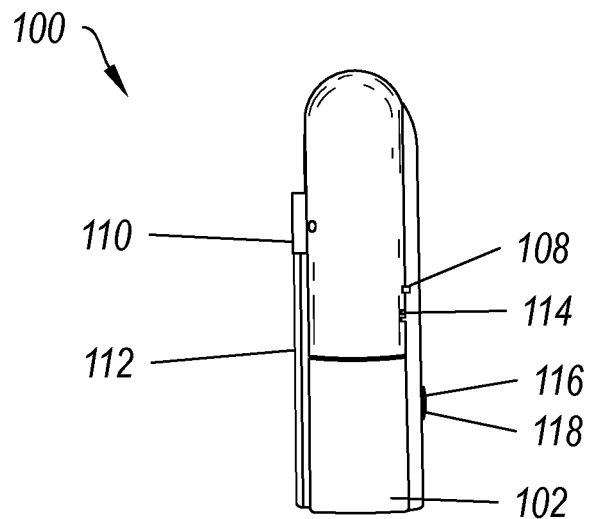
FIG. 1E illustrates a side view of the example of a wall mountable essential oil diffuser (the side views thereof being symmetrical)
Figure 1F:
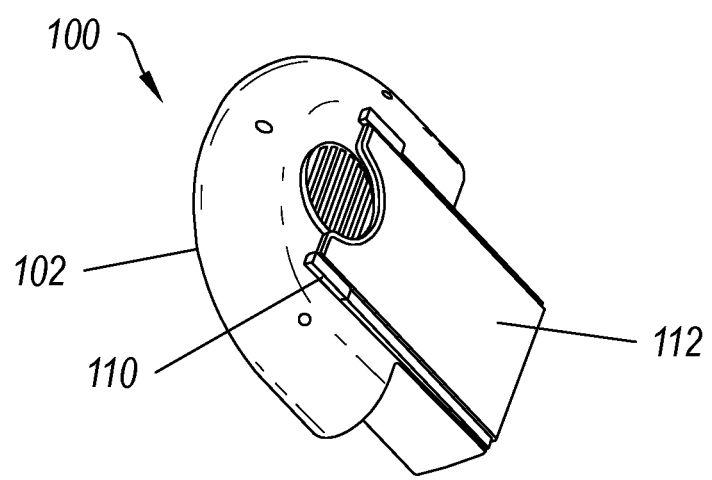
FIG. 1F illustrates a top left rear perspective view of the example of a wall mountable essential oil diffuser.
Figure 1G:
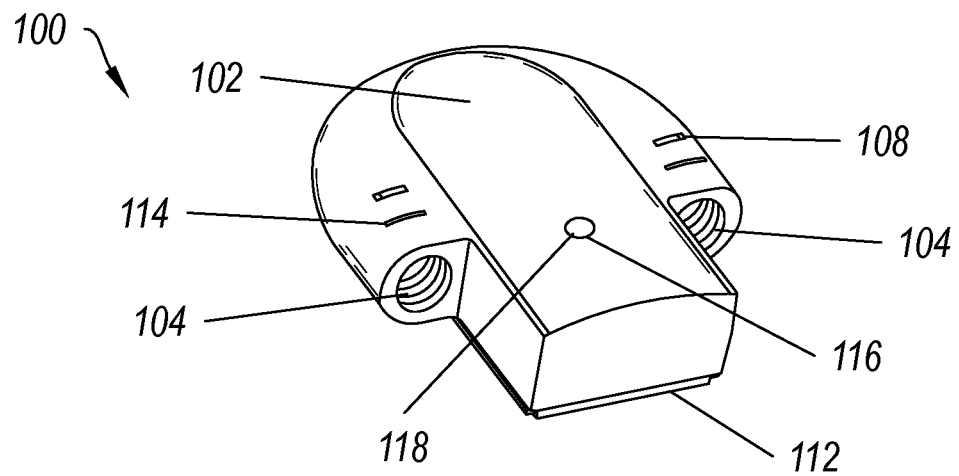
FIG. 1G illustrates a bottom right front perspective view of the example of a wall mountable essential oil diffuser.
Figure 1H:
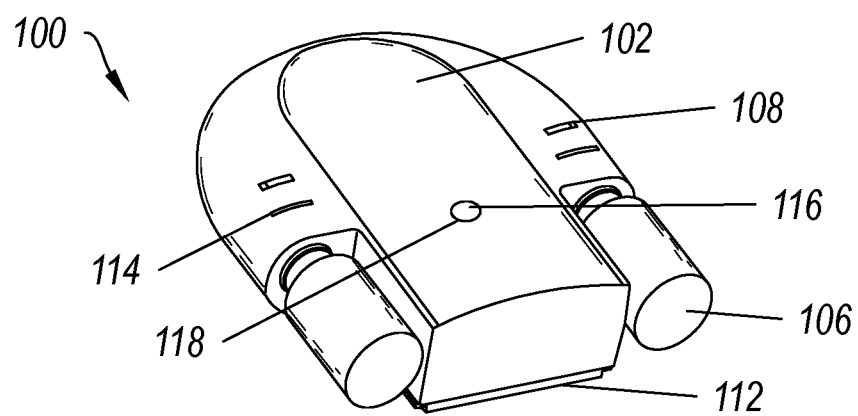
FIG. 1H illustrates a bottom right front perspective view of the example of a wall mountable essential oil diffuser with essential oil containers attached.
Figure 1I:
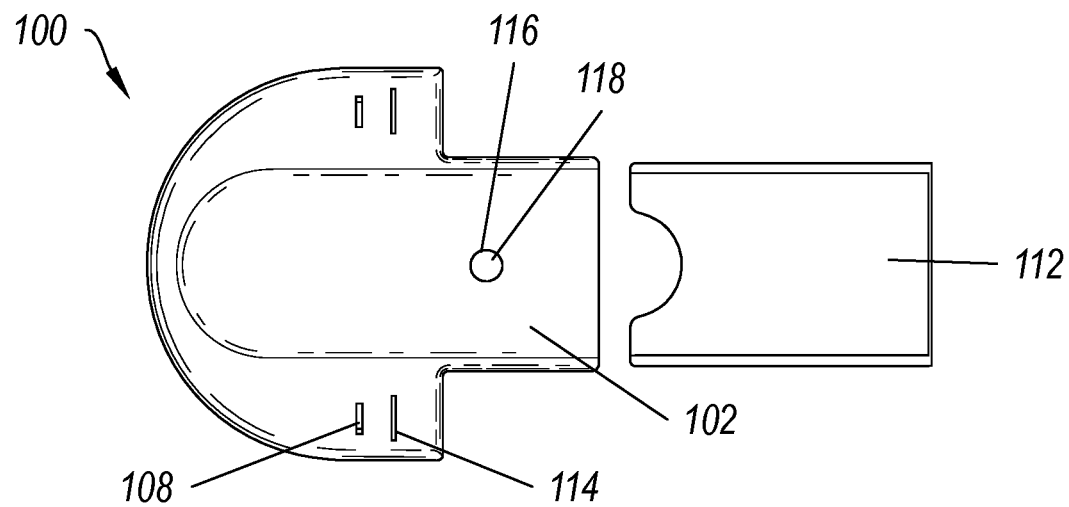
FIG. 1I illustrates an expanded front view of the example of a wall mountable essential oil diffuser.
Figure 1J:
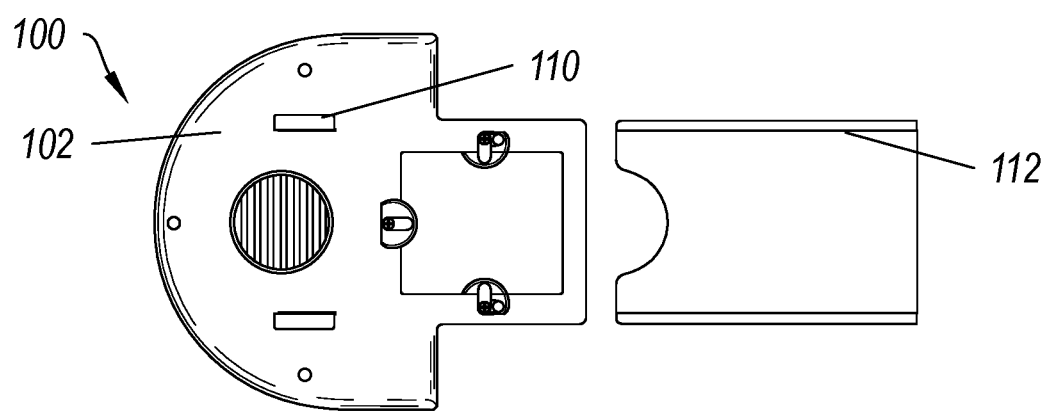
FIG. 1J illustrates an expanded rear view of the example of a wall mountable essential oil diffuser.

FIGS. 1A-1J (collectively "FIG. 1") illustrate an example of a wall mountable essential oil diffuser 100. FIG. 1A illustrates a front view of the example of a wall mountable essential oil diffuser 100; FIG. 1B illustrates a rear view of the example of a wall mountable essential oil diffuser 100; FIG. 1C illustrates a top view of the example of a wall mountable essential oil diffuser 100; FIG. 1D illustrates a bottom view of the example of a wall mountable essential oil diffuser 100; FIG. 1E illustrates a side view of the example of a wall mountable essential oil diffuser 100 (the side views thereof being symmetrical); FIG. 1F illustrates a top left rear perspective view of the example of a wall mountable essential oil diffuser 100; FIG. 1G illustrates a bottom right front perspective view of the example of a wall mountable essential oil diffuser 100; FIG. 1H illustrates a bottom right front perspective view of the example of a wall mountable essential oil diffuser 100 with essential oil containers attached; FIG. 1I illustrates an expanded front view of the example of a wall mountable essential oil diffuser; and FIG. 1J illustrates an expanded rear view of the example of a wall mountable essential oil diffuser. The wall mountable essential oil diffuser 100 can be used to disperse essential oil vapor throughout a desired area, such as a shower.

FIG. 1 shows that the wall mountable essential oil diffuser 100 can include a housing 102. In at least one implementation, the housing 102 is configured to contain the other elements within the wall mountable essential oil diffuser 100. The housing 102 may be constructed of any desired material, such as plastic or metal. Additionally or alternatively, the housing 102 is configured to align the other components of the wall mountable essential oil diffuser 100. I.e., the housing 102 can allow the internal and external components of the wall mountable essential oil diffuser 100 to be installed and proper spacing to be maintained among the components. One of skill in the art will appreciate that the housing 102 may be waterproof for use in areas of high moisture, such as a shower. As used in the specification and the claims, the phrase "configured to" denotes an actual state of configuration that fundamentally ties recited elements to the physical characteristics of the recited structure. That is, the phrase "configured to" denotes that the element is structurally capable of performing the cited element but need not necessarily be doing so at any given time. Thus, the phrase "configured to" reaches well beyond merely describing functional language or intended use since the phrase actively recites an actual state of configuration.

The housing 102 may be sized to fit in a small area. This sizing can be critical to allow the wall mountable essential oil diffuser to be installed in personal areas, such as bathrooms and showers. For example, the housing can be between 12 and 18 centimeters tall (e.g., as measured vertically in FIG. 1A), 11 and 15 centimeters wide (e.g., as measured horizontally in FIG. 1A), and 3 and 5 centimeters deep (e.g., as measured vertically in FIG. 1C). In particular, the housing 102 can be approximately 15 centimeters tall, 13 centimeters wide, and 4 centimeters deep. As used in the specification and the claims, the term approximately shall mean that the value is within 10% of the stated value, unless otherwise specified.

FIG. 1 also shows that the wall mountable essential oil diffuser 100 can include one or more apertures 104. The one or more apertures allow a container 106 to be attached to the wall mountable essential oil diffuser 100. In particular, the one or more apertures 104 can be sized and spaced to receive essential oil bottles. Each essential oil bottle is a standard, with a diameter of approximately 2 centimeters and threads with a spacing of approximately 8.5 threads per inch (tpi) and a total thread height of approximately 1 centimeter. Thus, a complimentary aperture 104 makes it easy for consumer to change the essential oil being diffused.

FIG. 1 further shows that the wall mountable essential oil diffuser 100 can include a switch 108. The switch 108 allows a user to select among the essential oil containers 106. For example, in the embodiment shown in FIG. 1 there are two apertures 104 and, therefore, two containers 106 may be inserted. The switch may allow a user to select either the essential oil in the first container 106, the second container 106 or both simultaneously. One of skill in the art will appreciate that the switch 108 can include a series of switches. For example, the switch 108 can include a first switch controlling whether the essential oil in the first container 106 is diffused, and a second switch controlling whether the essential oil in the second container 106 is diffused. One of skill in the art will further appreciate that the switch 108 can be mechanical or electronic. In addition, the switch 108 can be a button, either an electronic button or a mechanical push button, or a slider switch.

FIG. 1 additionally shows that the wall mountable essential oil diffuser 100 can include a wall dock 110. The wall dock 110 can mount to a variety of surfaces using a variety of mechanisms. For example, the wall dock 110 can attach to tile or other surfaces. The wall dock 110 includes an opening configured to receive at least a portion of the housing 102. For example, the housing 102 may have a protrusion which slides into a slot in the wall dock 110. Thus, the wall dock 110 can remain in place even as the housing 102 is moved when desired.

FIG. 1 moreover shows that the wall mountable essential oil diffuser 100 can include an attachment mechanism 112 on the wall dock 110. The attachment mechanism 112 can include any desired means for attaching the wall dock 110 to a vertical surface. For example, the attachment mechanism 112 can include suction cups, adhesive, polyurethane gel or any other desired attachment mechanism.

FIG. 1 further shows that the wall mountable essential oil diffuser 100 can include an outlet 114. The outlet 114 allows the air/essential oil mixture to exit the housing 102 and enter the environment. I.e., the fan blows air out of the housing 102 via the outlet 114. One of skill in the art will appreciate that a single outlet 114 can receive air flow from a fan at each aperture 104 or that each fan can move air through an independent outlet 114.

FIG. 1 additionally shows that the wall mountable essential oil diffuser 100 can include one or more lights 116. The one or more lights can act as a night light or produce light effects. For example, the one or more lights 116 can turn on when a motion sensor determines that someone is present. Thus, a user can have a low level of light. Additionally or alternatively, the presence or absence of power to the one or more lights 116 can allow a user to visually inspect whether the wall mountable essential oil diffuser 100 is operating properly.

FIG. 1 moreover shows that the wall mountable essential oil diffuser 100 can include a power button 118 (in the implementation of FIG. 1, the power button is made of a plastic which allows light to show through the power button 118, allowing it to be both the power button 118 and the light 116). The power button 118 can allow a user to control whether electrical power is being sent to the fan 202, the lights 116 or any other component that requires electrical power (such as an ultrasonic pad, as described below).

Additionally or alternatively, the wall mountable essential oil diffuser 100 can include a motion sensor. The motion sensor can be used to automate control of the wall mountable essential oil diffuser 100. For example, if the wall mountable essential oil diffuser 100 is installed in a bathroom, then the motion sensor can ensure that essential oils are being circulated only when a person is present. This can save energy as the wall mountable essential oil diffuser 100 will only run when needed.

Figure 2:
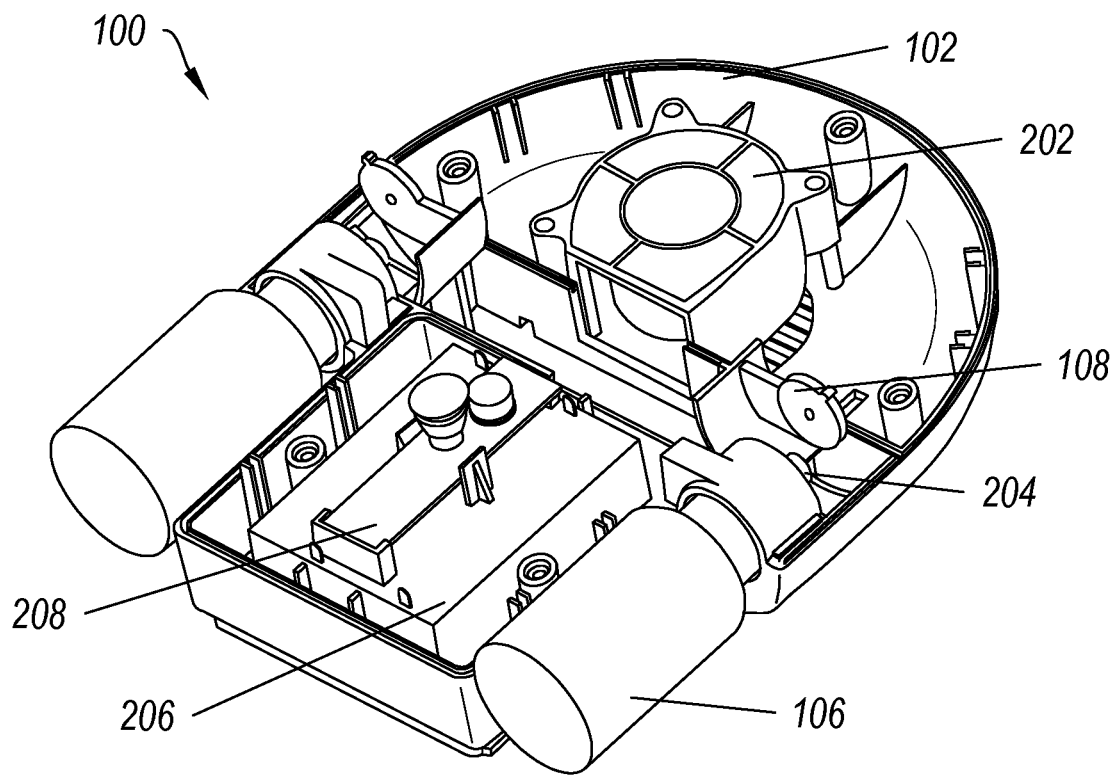
FIG. 2 illustrates an example of a cutaway view of the wall mountable essential oil diffuser.

FIG. 2 illustrates an example of a cutaway view of the wall mountable essential oil diffuser 100. Many sensitive and/or electrical components are covered by the housing 102. The housing 102 prevents these components from being damaged. In particular, the housing can be waterproof to protect internal components from coming in contact with water which can cause damage or electrical shorts.

FIG. 2 shows that the wall mountable essential oil diffuser 100 can include a fan 202. The fan 202 moves air into the essential oil containers. The air mixes with the evaporated oil in order to move the oil into the air. I.e., as oil evaporates into the air space on top of the oil, the fan moves that air into the environment and adds new air, which in turn receives evaporated essential oils. One of skill in the art will appreciate that one or more fans may be present for each aperture 104. That is, each essential oil container can have air flow directed by a dedicated fan 202.

One of skill in the art will appreciate that other methods of diffusing the essential oils are contemplated herein. For example, ultrasonic diffusion may be used. An ultrasonic diffuser is one that uses high-frequency sound vibrations to produce an extra fine essential oil mist that is then diffused to the surrounding environment. In particular, a wick/filter tube (cotton or similar material) is placed in the essential oil container. The essential oil then moves up the tube via osmosis to the top of the tube. The top of the tube is in contact with an ultrasonic diffuser panel which then vibrates at ultrasonic frequencies and transforms the oil into a mist which then is dispersed to the environment (either through ambient air movement or artificially, such as with a blower fan). An ultrasonic diffuser will generally produce more vaporization than an equivalently sized fan 202 and different diffusion methods may, therefore, be used depending on how quickly the essential oils should be diffused.

FIG. 2 also shows that the wall mountable essential oil diffuser 100 can include a wick 204 in the essential oil container 106. The wick 204 is a strip of porous material up which the essential oil is drawn by capillary action out of the container 106 nearer to the outlet. In addition, the wick 204 provides a larger surface area for evaporation. I.e., the wick 204 increases the diffusion rate of the essential oil out of the container 106.

FIG. 2 further shows that a portion of the housing 102 directs air from the fan 202 to the container. The switch 108 in a first position blocks the air being moved by the fan 202 from reaching the container 106 and in a second position allows the air being moved by the fan 202 to enter the container 106. Thus, when the switch 108 is in the first ("off") position no (or very little) diffusion occurs and when the switch 108 is in the second ("on") position a larger amount of diffusion occurs.

FIG. 2 additionally shows that the wall mountable essential oil diffuser 100 can include a power supply 206. The power supply 206 can include any desired power source, such as a plug or one or more batteries. Batteries may be removable (for replacement) or can be rechargeable, either separately or via a cord and port for charging while in the power supply 206.

FIG. 2 moreover shows that the wall mountable essential oil diffuser 100 can include a circuit board 208 or other electronics to control the operation of the fans 202, motion sensor, lights 116 or any other desired components. In particular, the circuit board 208 can include logic circuits, such as processors, and/or electrical wiring that allows power to be supplied to one or more electrical components when desired.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A wall mountable essential oil diffuser, the wall mountable essential oil diffuser comprising:
   a housing;
   a wall dock, wherein the wall dock is configured to:
      attach to a surface; and
      releasably receive at least a portion of the housing;

an aperture, wherein the aperture is configured to receive an essential oil container;
means for vaporizing the essential oil in the container, wherein the means for vaporizing the essential oil in the container is configured to increase the vaporization rate of essential oil within the essential oil container;
an outlet, wherein the outlet is configured to receive the vaporized essential oil and allow the vaporized essential oil to exit the housing;
a switch, wherein the switch is configured to allow a user to turn on and off the means for vaporizing the essential oil in the container;
a power supply, wherein the power supply is configured to provide power to at least the means for vaporizing the essential oil in the container; and
a power button, wherein the power button is configured to control whether the power supply is sending power to at least the means for vaporizing the essential oil.

2. The wall mountable essential oil diffuser of claim 1, wherein the housing is between 11 and 15 centimeters wide.

3. The wall mountable essential oil diffuser of claim 2, wherein the housing is approximately 13 centimeters wide.

4. The wall mountable essential oil diffuser of claim 1, wherein the housing is between 12 and 18 centimeters tall.

5. The wall mountable essential oil diffuser of claim 4, wherein the housing is approximately 15 centimeters tall.

6. The wall mountable essential oil diffuser of claim 1, wherein the housing is between 3 and 5 centimeters deep.

7. The wall mountable essential oil diffuser of claim 6, wherein the housing is approximately 4 centimeters deep.

8. The wall mountable essential oil diffuser of claim 1, wherein a diameter of at least one of the one or more apertures is approximately 2 centimeters.

9. The wall mountable essential oil diffuser of claim 1, wherein the aperture includes threading.

10. The wall mountable essential oil diffuser of claim 9, wherein the threading has a spacing of approximately 8.5 threads per inch.

11. The wall mountable essential oil diffuser of claim 9, wherein the total thread height is approximately 1 centimeter.

12. The wall mountable essential oil diffuser of claim 1, wherein the means for vaporizing the essential oil in the container includes an ultrasonic diffuser.

13. A wall mountable essential oil diffuser, the wall mountable essential oil diffuser comprising:
a housing, wherein the housing is waterproof;
a wall dock, wherein the wall dock is configured to:
attach to a surface using an attachment mechanism; and
releasably receive at least a portion of the housing;
a first aperture, wherein the first aperture:
is configured to receive a first essential oil container; and
includes threading;
a second aperture, wherein the second aperture:
is configured to receive a second essential oil container; and
includes threading;
a fan, wherein the fan is configured to move air through:
the first aperture and into the first essential oil container;
the second aperture and into the second essential oil container;
a first outlet, wherein the first outlet is configured to receive a first mixture of air and vaporized essential oil and allow the first mixture to exit the housing; and
a second outlet, wherein the second outlet is configured to receive a second mixture of air and vaporized essential oil and allow the second mixture to exit the housing;
a first switch, wherein the switch is configured to allow a user to determine whether air from the fan moves through the first aperture and into the first essential oil container;
a second switch, wherein the second switch is configured to allow a user to determine whether air from the fan moves through the second aperture and into the second essential oil container;
a power supply, wherein the power supply is configured to provide power to at least the fan;
a circuit board, wherein the circuit board controls the operation of the fan; and
a power button, wherein the power button is configured to control whether the power supply is sending power to at least the fan.

14. The wall mountable essential oil diffuser of claim 13, wherein the attachment mechanism includes suction cups.

15. The wall mountable essential oil diffuser of claim 13, wherein the attachment mechanism includes polyurethane gel.

16. The wall mountable essential oil diffuser of claim 13, wherein the first switch includes a button.

17. The wall mountable essential oil diffuser of claim 13, wherein the first switch includes a slider.

18. A wall mountable essential oil diffuser, the wall mountable essential oil diffuser comprising:
a housing, wherein the housing is waterproof;
a wall dock, wherein the wall dock is configured to:
attach to a surface; and
mate with at least a portion of the housing;
one or more protrusions on the housing, wherein the one or more protrusions are configured to mate with at least a portion of the wall dock;
a first aperture, wherein the first aperture:
is configured to receive a first essential oil container; and
includes threading;
a second aperture, wherein the second aperture:
is configured to receive a second essential oil container; and
includes threading;
the first essential oil container, wherein at least a portion of the first essential oil container is inserted in the first aperture;
a first wick, wherein the first wick extends though the first aperture into the first essential oil container;
the second essential oil container, wherein at least a portion of the second essential oil container is inserted in the second aperture;
a second wick, wherein the second wick extends though the second aperture into the second essential oil container;
a first fan, wherein the first fan is configured to move air through:
the first aperture and into the first essential oil container;
a second fan, wherein the second fan is configured to move air through:
the second aperture and into the second essential oil container;
a first outlet, wherein the first outlet is configured to receive a first mixture of air and vaporized essential oil and allow the first mixture to exit the housing; and a second outlet, wherein the second outlet is configured to receive a second mixture of air and vaporized essential oil and allow the second mixture to exit the housing;

a first switch, wherein the switch is configured to allow a user to determine whether air from the first fan moves through the first aperture and into the first essential oil container; and a second switch, wherein the second switch is configured to allow a user to determine whether air from the second fan moves through the second aperture and into the second essential oil container;

a motion sensor, wherein the motion sensor prevents operation of the first fan and the second fan unless motion is detected;

a power supply, wherein the power supply is configured to provide power to at least the first fan, the second fan, and the motion sensor;

a circuit board, wherein the circuit board controls the operation of the first fan, the second fan, and the motion sensor; and a power button, wherein the power button is configured to control whether the power supply is sending power to at least the fan.

19. The wall mountable essential oil diffuser of claim 18 further comprising:

one or more lights.

20. The wall mountable essential oil diffuser of claim 19, wherein:

at least one of the one or more lights are integrated into the power button; and at least one of the one or more lights turn on when the first fan is turned on.

\* \* \* \* \*